(12) United States Patent
Fukami

(10) Patent No.: US 11,384,373 B2
(45) Date of Patent: Jul. 12, 2022

(54) METHOD FOR PRODUCING SUGAR CARBOXYLIC ACID

(71) Applicant: San-ei Sucrochemical Co., Ltd., Chita (JP)

(72) Inventor: Ken Fukami, Chita (JP)

(*) Notice: Subject to any disclaimer, the term of this patent is extended or adjusted under 35 U.S.C. 154(b) by 0 days.

(21) Appl. No.: 16/968,117

(22) PCT Filed: Feb. 20, 2019

(86) PCT No.: PCT/JP2019/006412
§ 371 (c)(1),
(2) Date: Aug. 6, 2020

(87) PCT Pub. No.: WO2019/163853
PCT Pub. Date: Aug. 29, 2019

(65) Prior Publication Data
US 2021/0180099 A1    Jun. 17, 2021

(30) Foreign Application Priority Data

Feb. 20, 2018 (JP) .............................. JP2018-028044
Oct. 31, 2018 (JP) .............................. JP2018-205853

(51) Int. Cl.
*C12P 19/12* (2006.01)
*C12P 19/04* (2006.01)

(52) U.S. Cl.
CPC .............. *C12P 19/12* (2013.01); *C12P 19/04* (2013.01)

(58) Field of Classification Search
CPC .. C12Y 101/03; C12Y 111/01006; C12P 7/02; C12P 19/12; C12P 19/04
See application file for complete search history.

(56) References Cited

U.S. PATENT DOCUMENTS

| | | | |
|---|---|---|---|
| 4,345,031 A | 8/1982 | Coppens | |
| 5,897,995 A | 4/1999 | Vroemen et al. | |
| 2004/0253345 A1 | 12/2004 | Anthonius et al. | |
| 2007/0154595 A1 | 7/2007 | Budtz et al. | |
| 2015/0232813 A1 | 8/2015 | Nagaya et al. | |

FOREIGN PATENT DOCUMENTS

| | | |
|---|---|---|
| EP | 1753297 A2 | 2/2007 |
| JP | 5599194 A | 7/1980 |
| JP | H0584074 A | 4/1993 |
| JP | 10502825 A | 3/1998 |
| JP | 2000502904 A | 3/2000 |
| JP | 2001245657 A | 9/2001 |
| JP | 3310008 B2 | 7/2002 |
| JP | 2003093090 A | 4/2003 |
| JP | 2005504554 A | 2/2005 |
| JP | 2007028917 A | 2/2007 |
| JP | A2007535331 A | 12/2007 |
| JP | 4417550 B2 | 12/2009 |
| JP | 2011502511 A | 1/2011 |
| JP | 6321857 * | 5/2018 ............. C12P 19/02 |
| JP | 6321857 B1 | 5/2018 |
| WO | WO9724454 A1 | 7/1997 |
| WO | WO9931990 A1 | 7/1999 |
| WO | WO2009016049 A1 | 2/2009 |
| WO | WO20090061571 A1 | 5/2009 |
| WO | WO2010/106170 A1 | 9/2010 |
| WO | WO2014042237 A1 | 3/2014 |

OTHER PUBLICATIONS

Dabb L., Calcium Carbonate Dissolution and Precipitation in Water: Factors Affecting the Carbonate Saturometer Method. M. Sc., Thesis, 1971, Utah State Univ., pp. 1-46. (Year: 1971).*
Fukami et al., Effect of Water Content on the Glass Transition Temperature of Calcium Maltobionate and its Application to the Characterization of Non-Arrhenius Viscosity Behavior. Food Biophys., 2016, vol. 11: 410-416; published online Nov. 27, 2016. (Year: 2016).*
Notice of Reasons for Rejection issued to JP Application No. 2018-028044, dated Apr. 20, 2018.
Notice of Reasons for Rejection issued to JP Application No. 2018-205853, dated Jan. 9, 2019.
Fan Z. et al., "Characterization of Kinetics and Thermostability of Acremonium glucooligosaccharide Oxidase", Biotechnol. Bioeng., 2010, vol. 68, No. 2, pp. 231-237.
Extended European Search Report issued in the EP Patent Application No. 19758227.3, dated Mar. 2, 2021.

* cited by examiner

*Primary Examiner* — Ganapathirama Raghu
(74) *Attorney, Agent, or Firm* — Muncy, Geissler, Olds & Lowe, P.C.

(57) ABSTRACT

To provide a method for industrially producing a sugar carboxylic acid from an oxidized starch decomposition product or oxidized transfer reaction product having a degree of polymerization of 2 or more in a high yield, using a catalase formulation which quickly decomposes hydrogen peroxide produced as a by-product in the oxidation. A method for producing a sugar carboxylic acid in which an aldehyde group on a reducing end of a starch decomposition product or starch transfer reaction product having a degree of polymerization of 2 or more and having a glucose residue at the reducing end is oxidized, the method comprising a step of treating a raw material substrate containing the starch decomposition product or starch transfer reaction product in the presence of a catalase formulation with a carbohydrate oxidase agent producing hydrogen peroxide as a by-product in carbohydrate oxidation, wherein a total volume of a reaction liquid in the treatment step is 1 L or more, wherein a predetermined amount of a basic compound is added during the treatment step; and wherein a carbonate or a hydrogen carbonate is added as the basic compound in an amount by mass corresponding to 5% or more of the predetermined amount at a start of the treatment step.

16 Claims, No Drawings

METHOD FOR PRODUCING SUGAR CARBOXYLIC ACID

TECHNICAL FIELD

The present invention relates to a method for producing a sugar carboxylic acid, a salt thereof or a lactone thereof, in which an aldehyde group on a reducing end of a starch decomposition product or starch transfer reaction product having a degree of polymerization of 2 or more and having a glucose residue at the reducing end is oxidized.

BACKGROUND ART

Gluconic acid, which is one of aldonic acids obtained by oxidizing the reducing end of glucose, is used as a mineral supplementing agent because of having not only function of selectively growing bifidobacteria, but also a characteristic of forming stable salts with inorganic cations such as calcium, despite being a monosaccharide. However, gluconic acid had a disadvantage that solution stability thereof is poor, and when stored at a high concentration, it precipitates from solution.

Materials that compensate for these drawbacks include sugar carboxylic acids, such as maltobionic acid, in which glucose is bonded to a non-reducing end of gluconic acid. Maltobionic acid, which is a sugar carboxylic acid, also forms stable salts with inorganic cations, but has excellent solubility and features of not precipitating even when stored under high concentration conditions. As described above, oxidation of a reducing end of a carbohydrate such as a disaccharide or a higher polysaccharide is expected to produce many functional substances.

Patent Documents 1 and 2 disclose a method of using microorganisms belonging to genus *Acinetobacter*, genus *Burkholderia*, genus *Gluconobacter*, genus *Acetobacter*, etc. as a method of oxidizing maltose, lactose, cellobiose, and the like having a degree of polymerization of 2. As an enzymatic technique for oxidizing a starch decomposition product having a degree of polymerization of 4 or more, a technique using a carbohydrate oxidase formulation derived from a microorganism belonging to genus *Microdochium* or a carbohydrate oxidase formulation derived from a microorganism belonging to genus *Acremonium* has been known.

Patent Document 1: Japanese Unexamined Patent Application, Publication No. 2001-245657
Patent Document 2: Japanese Unexamined Patent Application, Publication No. 2007-028917
Patent Document 3: Japanese Patent No. 4417550
Patent Document 4: Japanese Patent No. 3310008
Patent Document 5: Pamphlet of PCT International Publication No. WO2014/042237
Patent Document 6: Japanese Unexamined Patent Application (Translation of PCT Application), Publication No. 2000-502904

DISCLOSURE OF THE INVENTION

Problems to be Solved by the Invention

The carbohydrate oxidases of Patent Documents 3 to 5 generate hydrogen peroxide as a by-product in a reaction for oxidizing carbohydrates. Hydrogen peroxide is capable of denaturing proteins, as can be seen in applications such as a disinfectant agent or a bleaching agent, and hydrogen peroxide produced as a by-product during carbohydrate oxidation denatures and deactivates carbohydrate oxidases. Therefore, rapid decomposition of hydrogen peroxide is necessary in order to industrially stably and efficiently oxidize a starch decomposition product and starch transfer reaction product having a degree of polymerization of 2 or more, using a carbohydrate oxidase.

In the glucose oxidase formulation of Patent Document 6, hydrogen peroxide is also generated in the process of oxidizing glucose to gluconic acid. It is disclosed to use a catalase formulation as a production technique for rapidly decomposing by-product hydrogen peroxide.

Moreover, Patent Document 6 discloses a technique of continuously maintaining the pH of the reaction solution within a constant range in the process of oxidizing glucose to gluconic acid. As a general technique for maintaining the pH of a reaction solution constant, a technique for keeping the pH of an entire reaction solution constant by adding a pH buffer is known.

When a starch decomposition product or starch transfer reaction product having a degree of polymerization of 2 or more is oxidized, addition of a catalase formulation together with a carbohydrate oxidase also enables hydrogen peroxide produced as a by-product during carbohydrate oxidation to be quickly decomposed. However, although the cause is unclear, an oxide having a degree of polymerization of 2 or more cannot be stably produced in a high yield.

The present invention has been made in view of the above circumstances, and the present invention provides a method for industrially producing a sugar carboxylic acid from an oxidized starch decomposition product or oxidized transfer reaction product having a degree of polymerization of 2 or more in a high yield, using a catalase formulation which quickly decomposes hydrogen peroxide produced as a by-product in the oxidation. In particular, it is an object of the present invention to provide a method for industrially producing a sugar carboxylic acid in a high yield using a reaction solution having a large volume of 1 L or more.

Means for Solving the Problems

The present inventors have studied the oxidation of a starch decomposition product or starch transfer reaction product with a degree of polymerization of 2 or more as a raw material, using various scales of containers from beakers, flask-level containers to batches, large reactor-level containers, and have found that performing oxidation of reaction solution of 1 L or more containing a raw material in a large-volume container reduces yield, and that in order to obtain a desired yield, the reaction time tends to be long. Upon examining a cause therefor, it was found that an inside of a reaction solution held in a large-volume container is not uniform, and the progress state of the reaction was different between the vicinity of the surface and the inside. However, although use of conventional techniques such as stirring, circulating, and keeping the pH of the reaction constant improves the yield to some extent, it has been found that such improvement was still insufficient for yield and reaction time required for industrial production level.

In order to achieve the yield and reaction time required for industrial production levels, the present inventors have discovered that it is effective not to make the inner portion of the reaction solution chemically uniform or timewisely uniform, but rather to place the inner portion of the reaction solution in a predetermined non-uniform state.

It has also been discovered that hydrolysis by starch-degrading enzymes such as α-glucosidase and glucoamylase, which are impure enzymes contained in a catalase formulation, is a cause of destabilized production of an oxidized saccharide with a degree of polymerization of 2 or more, and that impure enzymes, if in a predetermined amount, allow the catalase formulation to be used in industrial production.

Based on these findings, the present inventors have completed the present invention. More specifically, the present invention provides the following.

A first aspect of the present invention is a method for producing a sugar carboxylic acid in which an aldehyde group on a reducing end of a starch decomposition product or starch transfer reaction product having a degree of polymerization of 2 or more and having a glucose residue at the reducing end is oxidized, the method comprising a step of treating a raw material substrate containing the starch decomposition product or starch transfer reaction product in the presence of a catalase formulation with a carbohydrate oxidase agent producing hydrogen peroxide as a by-product in carbohydrate oxidation, in which a total volume of a reaction liquid in the treatment step is 1 L or more, in which a predetermined amount of a basic compound is added during the treatment step; and in which a carbonate or a hydrogen carbonate is added as the basic compound in an amount by mass corresponding to 5% or more of the predetermined amount at a start of the treatment step.

A second aspect of the present invention is the method for producing a sugar carboxylic acid as descried in the first aspect, in which the carbonate or the hydrogen carbonate is added in the predetermined amount only at the start of the treatment step.

A third aspect of the present invention is the method for producing a sugar carboxylic acid as descried in the first aspect, in which addition of the basic compound in the predetermined amount comprises addition of a first basic compound which is a carbonate or a hydrogen carbonate in an amount by mass corresponding to 5% or more and less than 100% of the predetermined amount, at the start of the treatment step, and addition of a second basic compound that is identical to or is different from the first basic compound in an amount by mass corresponding to a remaining amount obtained by subtracting an amount added at the start of the treatment step from the predetermined amount, during the treatment step at a time other than at the start of the treatment step.

A fourth aspect of the present invention is the method for producing a sugar carboxylic acid as described in any one of the first to third aspects, in which the carbonate has a solubility in water more than zero and 0.01 mol/L or less.

A fifth aspect of the present invention is the method for producing a sugar carboxylic acid in which an aldehyde group on a reducing end of a starch decomposition product or starch transfer reaction product having a degree of polymerization of 2 or more and having a glucose residue at the reducing end is oxidized, the method comprising a step of treating a raw material substrate containing the starch decomposition product or starch transfer reaction product in the presence of a catalase formulation with a carbohydrate oxidase agent producing hydrogen peroxide as a by-product in carbohydrate oxidation, in which a total volume of a reaction liquid in the treatment step is 1 L or more, in which a predetermined amount of a basic compound is added during the treatment step; and in which a basic compound having a pKb of 1 or more and 8 or less is added as the basic compound in an amount by mass corresponding to 5% or more of the predetermined amount at a start of the treatment step.

A sixth aspect of the present invention is the method for producing a sugar carboxylic acid as described in the fifth aspect, in which the basic compound having a pKb of 1 or more and 8 or less is added in the predetermined amount only at the start of the treatment step.

A seventh aspect of the present invention is the method for producing a sugar carboxylic acid as described in the fifth aspect, in which addition of the basic compound in the predetermined amount comprises addition of a first basic compound which has a pKb of 1 or more and 8 or less in an amount by mass corresponding to 5% or more and less than 100% of the predetermined amount, at the start of the treatment step, and addition of a second basic compound that is identical to or is different from the first basic compound in an amount by mass corresponding to a remaining amount obtained by subtracting an amount added at the start of the treatment step from the predetermined amount, during the treatment step at a time other than at the start of the treatment step.

An eighth aspect of the present invention the method for producing a sugar carboxylic acid as described in any one of the first to fourth aspects, in which the carbonate is calcium carbonate, magnesium carbonate, dolomite or eggshell calcium.

A ninth aspect of the present invention is the method for producing a sugar carboxylic acid as described in any one of the fifth to seventh aspects, in which the basic compound is sodium hydrogen carbonate, potassium hydrogen carbonate or ammonium hydrogen carbonate.

A tenth aspect of the present invention is the method for producing a sugar carboxylic acid as described in any one of the first to ninth aspects, in which oxygen is supplied during the treatment step so that a dissolved oxygen amount is 1 ppm or more.

An eleventh aspect of the present invention is the method for producing a sugar carboxylic acid as described in any one of the first to ninth aspects, in which oxygen is supplied so that a dissolved oxygen amount is 1 ppm or more in a time period during which oxidation ratio is from 0% to 50%, during the treatment step.

A twelfth aspect of the present invention is the method for producing a sugar carboxylic acid as described in any one of the first to eleventh aspects, in which a content ratio (B/A) of saccharification activity (B) with respect to catalase activity (A) in the catalase formulation is 0.00002 or more and 0.005 or less, and in which the saccharification activity is present in an amount of 0.9 U/g or less with respect to a reducing sugar in the raw material substrate.

A thirteenth aspect of the present invention is the method for producing a sugar carboxylic acid as described in any one of the first to eleventh aspects, in which a content ratio (B/A) of saccharification activity (B) with respect to catalase activity (A) in the catalase formulation is 0.005 or less, and the saccharification activity (B) is 0.1 U/ml or more, and in which the saccharification activity is present in an amount of 0.9 U/g or less with respect to a reducing sugar in the raw material substrate.

A fourteenth aspect of the present invention is the method for producing a sugar carboxylic acid as described in any one of the first to thirteenth aspects, in which a total amount of the reaction liquid in the treatment step is 50 kg or more.

A fifteenth aspect of the present invention is the method for producing a sugar carboxylic acid as described in the fourteenth aspect, in which the total amount of the reaction liquid in the treatment step is 1 ton or more.

A sixteenth aspect of the present invention is the method for producing a carboxylic acid as described in any one of the first to fifteenth aspects, in which the sugar carboxylic acid is maltobionic acid.

Effects of the Invention

The present invention allows high yield production of sugar carboxylic acids which are useful as a material for solubilizing a mineral component in food, pharmaceuticals, industrial fields, and the like. In particular, yields and production amounts suitable for industrial production can be easily obtained.

PREFERRED MODE FOR CARRYING OUT THE INVENTION

Although specific embodiments of the present invention are disclosed in detail below, the present invention is not limited to the following embodiments, and can be implemented with appropriate modifications within the scope of the object of the present invention. For portions in which descriptions are overlapping, descriptions may be omitted as appropriate, but the gist of the invention is not limited.

An embodiment of a first aspect of the present invention is a method for producing a sugar carboxylic acid in which an aldehyde group on a reducing end of a starch decomposition product or starch transfer reaction product having a degree of polymerization of 2 or more and having a glucose residue at the reducing end is oxidized, the method comprising a step of treating a raw material substrate containing the starch decomposition product or starch transfer reaction product in the presence of a catalase formulation with a carbohydrate oxidase agent producing hydrogen peroxide as a by-product in carbohydrate oxidation, in which a total volume of a reaction liquid in the treatment step is 1 L or more, in which a predetermined amount of a basic compound is added during the treatment step; and in which a carbonate or a hydrogen carbonate is added as the basic compound in an amount by mass corresponding to 5% or more of the predetermined amount at start of the treatment step.

Another embodiment of the present invention is a method for producing a sugar carboxylic acid in which an aldehyde group on a reducing end of a starch decomposition product or starch transfer reaction product having a degree of polymerization of 2 or more and having a glucose residue at the reducing end is oxidized, the method comprising a step of treating a raw material substrate containing the starch decomposition product or starch transfer reaction product in the presence of a catalase formulation with a carbohydrate oxidase agent producing hydrogen peroxide as a by-product in carbohydrate oxidation, in which a total volume of a reaction liquid in the treatment step is 1 L or more, in which a predetermined amount of a basic compound is added during the treatment step; and in which a basic compound having a pKb of 1 or more and 8 or less is added as the basic compound in an amount by mass corresponding to 5% or more of the predetermined amount at start of the treatment step.

Below, the configuration of the present invention is described in order. The present invention is a method for obtaining a sugar carboxylic acid by preparing a reaction solution containing a raw material carbohydrate in advance and oxidizing an aldehyde group on a reducing end contained in the raw material carbohydrate in a treatment step.

The sugar carboxylic acid produced by the production method of the present invention is as follows.

(Sugar Carboxylic Acids)

The sugar carboxylic acid produced using the inventive method is not particularly limited, and any sugar carboxylic acid is acceptable, so far as it is obtained by oxidizing an aldehyde group on a reducing end of a starch decomposition product or starch transfer reaction product having a degree of polymerization 2 or more, and preferably a degree of polymerization 4 or more. The degree of polymerization of a starch decomposition product or starch transfer reaction product may be, for example, from 2 to 100, and preferably from 4 to 100, etc. More specifically, examples of the sugar carboxylic acid include oxidized maltodextrin, oxidized powdered syrup, oxidized starch syrup, maltohexaonic acid, maltotetraonic acid, maltotrionic acid, maltobionic acid, oxidized isomaltodextrin, oxidized panose, isomaltotrionic acid, isomaltobionic acid, nigerobionic acid, cordibionic acid and the like. Among these, the sugar carboxylic acid may be a free acid, a lactone, or a salt thereof.

Salts of sugar carboxylic acids are not particularly limited, and include calcium salts, magnesium salts, potassium salts, sodium salts, zinc salts, iron salts, copper salts, and the like.

The reaction solution containing a raw material carbohydrate prepared in advance has the following configuration.

(Raw Material Carbohydrates)

Carbohydrates used as the raw material in the present invention are starch decomposition products or starch transfer reaction products each having a glucose residue in its reducing end and a degree of polymerization of 2 or more, and examples thereof include maltose, isomaltose, maltotriose, isomaltotriose, maltotetraose, maltohexaose, panose, maltooligosaccharides, isomaltooligosaccharides, starch syrup, powdered syrup, dextrins, branched dextrins, isomaltodextrins, and the like. Raw material carbohydrates need not have a single degree of polymerization, and may be a mixture of carbohydrates having different degrees of polymerization.

The concentration of a raw material carbohydrate at the time of production of a sugar carboxylic acid is preferably 10 to 50% (by weight), and more preferably 20 to 40% (by weight), in consideration of concentration in the purification process or the like. Note that in this specification, "% (by weight)" refers to a content (by mass) of a target component, and refers to a content of the carbohydrate in the liquid here.

(Carbohydrate Oxidase Formulations)

The carbohydrate oxidase formulation in the context of the present invention refers to a carbohydrate oxidase formulation which oxidizes a carbohydrate having a degree of polymerization 2 or more and having a glucose residue in a reducing end and which generates hydrogen peroxide as a by-product. Examples include a carbohydrate oxidase formulation derived from a microorganism belonging to the genus *Microdochium*, a carbohydrate oxidase formulation derived from a microorganism belonging to the genus *Acremonium*, and specifically, a carbohydrate oxidase derived from *Acremonium chrysogenum*.

In the production of sugar carboxylic acids, such as maltobionic acid, the carbohydrate oxidase is made to act in a content of preferably 1 U/g or more and 30 U/g or less and more preferably 2 U/g or more 20 U/g or less, with respect to the reducing sugar (wt %) in the raw material substrate.

Since the decomposition of hydrogen peroxide by a catalase formulation is performed sufficiently in the present invention, the carbohydrate oxidation can be performed at a sufficient rate in spite of an increase in hydrogen peroxide produced as a by-product. In addition, since decomposition of the starch decomposition product or starch transfer reaction product with a degree of polymerization of 2 or more as a raw material is suppressed due to saccharification activity, even when the carbohydrate oxidation is performed over a certain period of time, the yield is hardly lowered, so that an excessive amount of a carbohydrate oxidase is not required.

Enzyme activity of the carbohydrate oxidase of the present invention is measured as follows. 2 ml of 0.1 M monopotassium phosphate-sodium hydroxide buffer (pH 7.0) containing 0.15% (w/v) phenol and 0.15% (w/v) triton X-100, 0.5 ml of a 10% maltose monohydrate solution, 0.5 ml of a 25 U/ml peroxidase solution, and 0.1 ml of a 0.4% (w/v) 4-aminoantipyrine solution were mixed and incubated at 37° C. for 10 minutes, and then 0.1 ml of an enzyme solution was added to initiate the reaction. As the enzyme reaction progressed, carbohydrate oxidation activity was measured by measuring an increase in absorbance at a wavelength of 500 nm. Using the 0.1 M phosphate buffer solution (pH 7.0) as a blank, the activity was calculated based on the following equation, provided that an amount of enzyme required to oxidize 1 μmol of maltose monohydrate in one minute is 1 unit.

$$\text{Maltose oxidation activity(U/ml)} = \{(A5-A2)-(Ab5-Ab2)\} \times 2.218 \times n$$

A2 and A5: absorbances (analyte) at 2 minutes and 5 minutes, respectively, after the reaction start Ab2 and Ab5: absorbances (blank) at 2 minutes and 5 minutes, respectively, after reaction start n: dilution ratio of the enzyme solution (Catalase Formulation)

The catalase formulation in the context of the present invention includes a catalase formulation derived from microorganisms such as genus *Aspergillus* or genus *Micrococcus*, and specifically a catalase formulation derived from *Aspergillus niger* or *Micrococcus lysodeikticus*. Selection and use of a commercially available glucose oxidase formulation having catalase activity as a secondary activity is also included.

A catalase formulation often contains impure enzymes with saccharification activity such as glucoamylase and α-glucosidase. When a large amount of these impure enzymes is mixed, a raw material for a sugar carboxylic acid, that is, a starch decomposition product or starch transfer reaction product having a glucose residue in the reducing end and having a degree of polymerization of 2 or more, or a sugar carboxylic acid which is a reaction product of oxidation of these raw materials, is decomposed, and this makes it impossible to produce a sugar carboxylic acid with a stable quality. Therefore, a highly pure catalase formulation is generally desired.

For example, a catalase formulation containing almost no impure enzymes, such as a recombinant catalase formulation produced with purity increased by genetic recombination or a purified catalase formulation distributed as a reagent, can be used.

However, since addition of a neutralizing agent to a reaction solution by a predetermined method described below improves whole yield, even a catalase formulation containing impure enzymes in a certain range can be used without issue. As a result, there is also a cost advantage in industrial production. This catalase formulation containing impure enzymes in a predetermined range is described below.

(Neutralizing Agent)

The neutralizing agent in the context of the present invention is an agent which is used to adjust pH of a reaction solution, and is added to the reaction solution during the treatment step. As an example of the neutralizing agent, a basic compound can be used.

As for the basic compound, a carbonate, a hydrogen carbonate, or a hydroxide salt can be used as an example.

As an example, the carbonate has a solubility in water at 25° C. of more than 0 and 0.01 mol/L or less. For example, calcium carbonate, magnesium carbonate, dolomite, eggshell calcium, or the like can be used.

As the hydrogen carbonate, for example, sodium hydrogen carbonate, potassium hydrogen carbonate, ammonium hydrogen carbonate, or the like can be used.

As the hydroxide salt, for example, sodium hydroxide, calcium hydroxide, or the like can be used.

As another example of the basic compound, a basic compound which has a pKb of 0 or more and 8 or less in water as a solvent at 25° C. can be used. Basic compounds having a pKb greater than 8 have poor neutralizing function and are not suitable for use in industrial production. Typical examples of pKb using water as a solvent at 25° C. include pKb of 0 or more, greater than 0, 0.5 or more, 1 or more, greater than 1, 1.3 or more, greater than 1.3, 1.5 or more, 2 or more, 2.5 or more, 3 or more, 3.5 or more, 4 or more, or 4.5 or more, and 1 or less, less than 1, 1.5 or less, 2 or less, 3 or less, 4 or less, 4.5 or less, 5 or less, 5.5 or less, 6 or less, 6.5 or less, 7 or less, or 8 or less.

Examples of the basic compound with a pKb of 0 or more and 8 or less include sodium hydroxide, calcium hydroxide, sodium hydrogen carbonate, potassium hydrogen carbonate, ammonium hydrogen carbonate, ammonia and the like.

The total amount of the neutralizing agent to be added during the treatment step (including the start of the treatment step) can be calculated as an amount of the neutralizing agent required to neutralize the reducing sugar in the carbohydrate as a raw material. For example, if the neutralizing agent is a divalent ion, the number of moles required for neutralization is calculated so that the molar ratio of the reducing sugar in the carbohydrate as a raw material and the neutralizing agent is 2:1. When the neutralizing agent is a monovalent ion, the number of moles required for the neutralization is calculated so that the molar ratio is 1:1. In this specification, the "predetermined amount" of the neutralizing agent refers to an amount obtained by determining the total number of moles of the neutralizing agent required for neutralizing the reducing sugar in the carbohydrate as a raw material to be 100%. Additionally, the mass of the neutralizing agent used in the neutralization, which may be referred to herein as a corresponding mass, can be calculated by a conventional method from the number of moles required for the neutralization and the molecular weight of the neutralizing agent.

Even when a plurality of neutralizing agents is used, addition weight of each of the neutralizing agents can be calculated by proportionally dividing the above predetermined amount and using the molecular weight of each of the neutralizing agents. As an example, in a case of plural types of neutralizing agents being used, if a certain neutralizing agent X is to be made to act on a portion of Y % of the predetermined amount, the mass of the neutralizing agent X to be added can be calculated by (solid content of the saccharide raw material) [g]/(saccharide raw material average molecular weight)×(molecular weight of the neutralizing agent X)/(valence of ion of the neutralizing agent X)×(Y/100). Calculation is performed by substituting 2 in the above formula, as the valence of ion of the neutralizing agent, when the neutralizing agent generates divalent ions, and by substituting 1 in the above formula when the neutralizing agent generates monovalent ions.

Incidentally, during the treatment step of producing a sugar carboxylic acid, the pH of the reaction solution gradually decreases, and the pH of the reaction solution tends to change from neutral to acidic. Since it is known that the activity of carbohydrate oxidases is greatly reduced when the pH is less than 4, generally, the state of the reaction solution is constantly monitored by a pH sensor. It is common practice to set an arbitrarily desired target pH value between pH 4 and pH 7, and to add neutralizing agents sequentially from the start of the treatment step so that the pH is kept constant at the target pH value (real-time feedback-controlled sequential addition method).

However, in a reaction system with a total volume of the reaction solution being 1 L or more, the present inventors tried the real-time feedback-controlled sequential addition method but could not achieve a high yield of 90% or more. Upon examining various methods of adding the neutralizing agent, a high yield of 90% or more was achieved by adding an excessive amount of the neutralizing agent in advance at the start of the treatment step in anticipation of the pH falling during treatment step.

That is, the present invention comprises adding a certain amount of the neutralizing agent at the start of the treatment step. For example, an amount of 5% or more of the total moles of the neutralizing agent (i.e., predetermined amount) required throughout the entire duration of the reaction is added to the reaction solution at the start of the treatment step. Specifically, the mass of the neutralizing agent to be added can be calculated by a conventional method from the required number of moles and the molecular weight of the neutralizing agent to be used.

As described above, since the neutralizing agent may be added in an amount of 5% or more of the predetermined amount at the start of the treatment step, the amount added at the start of treatment step may be 100% of the predetermined amount (that is, the neutralizing agent may be added only at the start of treatment step), or the amount added at the start of the treatment step may be 5% or more and less than 100% of the predetermined amount.

When the amount added at the start of the treatment step is less than 100% of the predetermined amount, a remaining amount obtained by subtracting an amount of the neutralizing agent added at the start of the treatment step (amount of 5% or more of the predetermined amount) from the predetermined amount, i.e. an amount of 95% or less of the predetermined amount, is added during the treatment step at a time other than at the start of the treatment step. In this regard, the neutralizing agent to be added at a time other than at the start of the treatment step is selected from the above-mentioned basic materials, and may be the same as or different from the neutralizing agent added at the start of the treatment step.

Specifically, the mass of the neutralizing agent to be added as the remaining amount (sometimes referred to as mass corresponding to the remaining amount in this specification) can be calculated by a conventional method using the number of moles required for neutralizing the remainder and the molecular weight of the neutralizing agent to be added as the remaining amount. The number of times in which the remaining amount is added is not limited, and may be one or a plurality of times of addition (divided addition), but it is preferable that the number of times in which the remaining amount is added is small.

What is important is that the requirement that at the start of the treatment step, which corresponds to an initial stage of the reaction, it is essential to add 5% or more of the neutralizing agent in order to obtain a yield of 90% in the production in which the total volume of the reaction solution is 1 L or more. In this regard, as the neutralizing agent to be used at the start of the treatment step, specific basic compounds described below can be used.

On the other hand, manufacturing process is relatively flexible during the treatment step except for the start of the treatment step, and the neutralizing agent can be selected from the basic compounds described above. There are no particular restrictions on the method of addition. The addition method may be, for example, a method of adding a constant amount at regular time intervals, or a method of adding a necessary amount as appropriate to keep pH constant.

Typical examples of the amount of the neutralizing agent added at the start of treatment step are mass corresponding to 5% or more, 6% or more, 7% or more, 8% or more, 9% or more, 10% or more, 15% or more, 20% or more, 30% or more, 40% or more, or 50% or more, or 100% or less, less than 100%, 90% or less, 80% or less, or 70% or less of the predetermined amount.

(Neutralizing Agent Added at the Start of the Treatment Step)

As the neutralizing agent to be added at the start of the treatment step, specific basic compounds may be used, which may be sometimes referred to as a first basic compound.

As the basic compound, a carbonate or a hydrogen carbonate can be used as an example.

As an example, the carbonate has a solubility in water at 25° C. of more than 0 and 0.01 mol/L or less. For example, calcium carbonate, magnesium carbonate, dolomite, eggshell calcium, or the like can be used.

As the hydrogen carbonate, for example, sodium hydrogen carbonate, potassium hydrogen carbonate, ammonium hydrogen carbonate, or the like can be used.

As another example of the basic compound, a compound with a pKb in water as a solvent at 25° C. of greater than 1.3 and 8 or less can be used. Use of a compound with a pKb of 1.3 or less deactivates a carbohydrate oxidase immediately after addition, and carbohydrate oxidizing function cannot be restored, so that such a compound may not be used in some cases. A basic compound with a pKb greater than 8 is poor in neutralizing function and is not suitable for use in industrial production.

As a typical example of pKb, pKb in water as a solvent at 25° C. is greater than 1.3, 1.5 or more, 2 or more, 2.5 or more, 3 or more, 3.5 or more, 4 or more, or 4.5 or more and 1 or less, less than 1, 1.5 or less, 2 or less, 3 or less, 4 or less, 4.5 or less, 5 or less, 5.5 or less, 6 or less, 6.5 or less, 7 or less, or 8 or less.

Examples of the basic compound with a pKb of greater than 1.3 and 8 or less include sodium hydrogen carbonate, potassium hydrogen carbonate, ammonium hydrogen carbonate, and ammonia.

As described above, the specific basic compounds can be used as the neutralizing agent to be added at the start of the treatment step.

(Neutralizing Agents to be Added During the Treatment Step at a Time Other than at the Start of the Treatment Step)

On the other hand, a neutralizing agent (sometimes referred to as a second basic substance) to be added during the treatment step at a time other than at the start of the treatment step, is not limited to the above-mentioned specific basic substances (first basic substances), and can be widely selected from the above-mentioned basic compounds. That is, the neutralization agent (second basic substance) which is to be added during the treatment step at a time other than at the start of the treatment step, may be the same basic compound as the neutralizing agent (first basic substance) to be added at the start of the treatment step, or may be a different basic compound. When an addition amount at the start of the treatment step is less than 100% of the predetermined amount, a remaining amount of the neutralizing agent obtained by subtracting the amount of the neutralizing agent added at the start of the treatment step (amount of 5% or more of the predetermined amount) from the predetermined amount, i.e., amount of 95% or less of the predetermined amount, is added during the treatment step at a time other than at the start of the treatment step. Specifically, the mass of the neutralizing agent to be added as the remaining amount (sometimes referred to as mass corresponding to the remaining amount in this specification) can be calculated by a conventional method using the number of moles required for neutralizing the remainder and the molecular weight of the neutralizing agent to be added as the remaining amount. The number of times in which the remaining amount is added is not limited, and may be one or a plurality of times of addition (divided addition), but it is preferable that the number of times in which the remaining amount is added is small.

The reason why a higher yield can be obtained by the method in which an excessive amount of the neutralizing agent is added in advance at the start of the treatment step compared to a method in which the neutralizing agent is added sequentially from the start of the treatment step onward is not sufficiently clear. However, in a case of a reaction system in which the total volume of the reaction solution is 1 L or more, it is considered to be one of the causes that in the initial phase of the reaction, a concentration gradient of a reaction intermediate substance, a concentration gradient of a reaction product/by-product, a concentration gradient of an added neutralizing agent and the like tend to occur in the reaction solution.

Specifically, the first conjecture is that since the reaction solution containing a large amount of carbohydrates results in a high viscosity in the reaction solution, it takes time for the neutralizing agent to diffuse. It is speculated that a high concentration area of the neutralizing agent occurs around a point of addition (drop point) of the neutralizing agent in the reaction solution, but the pH is lowered outside the area until the neutralizing agent diffuses and becomes homogeneous, and activity of a carbohydrate oxidase temporarily decreases, so that the above-mentioned state is maintained until agitation progresses and the concentration gradient is resolved.

The second conjecture is that pH in an area other than the vicinity of the drop point is lowered before the neutralization agent diffuses and becomes homogeneous, the lowered pH damages the enzyme, and thus decrease in the activity is faster than in the case in which the neutralizing agent is added in advance, so that the yield becomes poor.

In any one of the conjectures, since the drop point provides influence over a long period of time, adding an excessive amount to some extent (5% or more) of a neutralizing agent at the start of the treatment step to reduce subsequent drop points, preferably only once at the start of the treatment step, rather than providing a plurality of drop points, such as every one hour during the treatment step, results in a relatively high total enzyme activity (time integral value), and this results in a high yield. Further, the reaction system is also considered to be a complicated reaction system through a plurality of intermediates.

Incidentally, adding an excessive amount of the neutralizing agent at the start of the treatment step means that the pH at the start of the treatment step becomes high. In this regard, it should be noted that if the reaction solution exhibits strong alkalinity, the carbohydrate oxidase instantaneously deactivates, and the carbohydrate oxidation function is not restored. However, the specific neutralizing agents to be used at the start of the treatment step can be used without deactivation of the carbohydrate oxidase even if the neutralizing agents are added at the start of the treatment step.

In addition, it has been found that the gradient of the concentration generated in the reaction system in which the total volume of the reaction solution is 1 L or more tends to become stronger as the total amount of the reaction solution increases. That is, as the volume of the reaction solution increases and the size of the reaction vessel increases, the yield tends to decrease. Therefore, in the production method of the present invention, the higher the volume of the reaction solution, the more the yield improvement effect is exhibited. For example, the present invention can be applied to a reaction system in which the total amount of the reaction solution is 50 kg or more. Further, the present invention can be applied to a reaction system of 100 kg or more, a reaction system of 500 kg or more, a reaction system of 1 ton or more, a reaction system of 10 tons or more and a reaction system of 50 tons or more, and can be preferably used in a reaction system of 100 tons or more and a reaction system of 500 tons or more.

Since the reaction solution preparation stage and the start of the treatment step are consecutive, addition of the neutralizing agent at the start of treatment step and addition of the neutralizing agent during the reaction solution preparation stage are substantially identical. Therefore, an embodiment in which the neutralizing agent is added during the reaction solution preparation stage is also included in the present invention.

In addition, although depending on the form (liquids, solids, etc.) and addition methods (dropwise, spraying, etc.) of the neutralizing agent, addition of the neutralizing agent requires a certain finite period of time. Therefore, an embodiment in which addition of the neutralizing agent is continuously performed over a time range from the reaction solution preparation stage to the start of the treatment step is also included in the present invention.

On the other hand, when the neutralizing agent is added to the reaction solution in an amount of 5% or more of the predetermined amount at the start of the treatment step and then the remaining amount (an amount of 95% or less of the predetermined amount) is added to the reaction solution during the treatment step, the time interval between the addition of the first neutralizing agent in an amount of 5% or more of the predetermined amount and the next addition of the neutralizing agent is required as a predetermined time interval. The predetermined time is typically 0.25 hours or more, 0.5 hours or more, or 1 hour or more. This predetermined time is considered to be time required as time during which the entire stirring of the reaction solution immediately after the reaction solution preparation stage progresses to some extent. The time required is typically 8 hours or less, 7 hours or less, 6 hours or less, 5 hours or less, 4 hours or less, 3 hours or less, 2 hours or less or 1 hour or less. This predetermined time depends on the amount of the neutralizing agent added at the start of the treatment step. When a sufficient amount of the neutralizing agent is added relative to the predetermined amount at the start of the treatment step, the predetermined time may be relatively long, and when a relatively small amount of the neutralizing agent to the predetermined amount is added at the start of the treatment step, the predetermined time is relatively short. This is because the neutralizing agent added at the start of the treatment step is consumed for neutralization during the treatment step.

As a method of additionally adding a neutralizing agent which is insufficient due to consumption of the neutralizing agent, there is also a method of controlling the neutralizing agent using the pH of the reaction solution in addition to the method of timewise controlling as described above. For example, a stable reaction can be achieved by monitoring the pH of the reaction solution during the progress of the treatment step and adding a subsequent neutralizing agent at a timing at which the pH shifts from a state in which the pH exceeds pH 6.0 to a state in which the pH is 6.0 or less.
(pH of the Reaction Solution in the Treatment Step)

The lower limit of the pH of the reaction solution in the treatment step is, for example, 5.0 or more, 6.0 or more, 7.0 or more, 8.0 or more or 9.5 or more, and the upper limit is, for example, 11.0 or less or 10.0 or less.
(Temperatures in the Treatment Step)

Reaction temperatures in the reaction step of a carbohydrate oxidase and catalase are preferably, for example, about 20 to 60° C., and more preferably, 25 to 40° C.
(Supply of Oxygen in the Treatment Step)

In the oxidation of the present invention, since oxygen is required for the reaction system, air or oxygen is preferably passed through the reaction system. In addition, since oxygen is consumed as a result of the reaction, it is necessary to supply a reaction solution from a region containing more oxygen to a region in which oxygen is deficient in the reaction solution. Therefore, it is preferable to constantly stir the reaction solution. Therefore, it is most desirable to stir the reaction solution at a predetermined rate under aeration of a predetermined amount of air or oxygen.

An amount of oxygen in a reaction solution can be measured by a dissolved oxygen sensor or the like as a so-called dissolved oxygen amount. Therefore, an amount of aeration and rate of agitation can be adjusted so that the dissolved oxygen amount becomes equal to or greater than a predetermined amount during the treatment. As shown in the examples described below, for example, a yield of 90% or more can be obtained by setting the dissolved oxygen amount to 1 ppm or more over the entire duration of the treatment step. The method is achieved, for example, by stirring while oxygen is aerated from an oxygen tank. Alternatively, it can be achieved by bubbling a reaction solution while aerating fine bubbles of air by passing the reaction solution through an air diffuser from an air compressor. Depending on the shape of the reaction vessel, this can also be achieved by a method of shear-supplying fine air bubbles, in which supplied air is subjected to high speed agitation by high-speed agitator such as a screw type agitator or a propeller type agitator. Note that the dissolved oxygen amount is a total dissolved oxygen amount including not only oxygen dissolved in the reaction solution by aeration but also oxygen, etc. generated by a catalase formulation during the reaction.

In addition, since the measurement of a dissolved oxygen amount in a reaction solution using a dissolved oxygen sensor is relatively easy, it is possible to design a manufacturing method which is commensurate with manufacturing costs required for industrial production. Specifically, the reaction rate during the treatment step is not necessarily constant, and in many cases the reaction rate tends to be high in the first half of the treatment step and slow in the second half. Since more oxygen is required in the first half in which the reaction rate is high, it is possible to stir while oxygen is aerated from an oxygen tank so that the dissolved oxygen amount becomes 1 ppm or more in the first half of the treatment step, and to decrease the aeration amount in the second half of the treatment step. As another example, it is possible to monitor the oxidation ratio of the reaction, to stir while aerating air so that the dissolved oxygen amount becomes 1 ppm or more during the treatment step in which the oxidation ratio is 0 to 50%, and to decrease the aeration amount during the treatment step in which the oxidation ratio is 51% or more. As described above, setting the dissolved oxygen amount to 1 ppm or more only during the treatment step in which the oxidation ratio is 0 to 50% enables a used amount of oxygen to be reduced, and this results in reduction in costs and burden on the process control.

The upper limit of the dissolved oxygen amount in the reaction solution is, for example, 30 ppm or less, preferably 15 ppm or less, and more preferably 7.5 ppm or less.

Since oxidation to sugar carboxylic acid can be confirmed from the reduction in the amount of reducing sugars, the oxidation ratio (%) can be measured by using, for example, a colorimetric determination method by Nelson-Somogyi method. In this case, the oxidation ratio (%) of the entire reaction system can be also calculated by quantifying the amount of reducing sugars by the Nelson-Somogyi method.

(Amount of reducing sugar before start of reaction−amount of reducing sugar in reaction solution)/amount of reducing sugar before start of reaction×100=oxidation ratio (%)

It can also be confirmed by analyzing the raw material carbohydrate or sugar carboxylic acid by HPLC. For example, after oxidizing maltose as a raw material, maltose and maltobionic acid can be quantified by measurement using HPAED-PAD method (pulsed amperometry detector, CarboPac PA1 column) under the following conditions: elution: 35° C., 1.0 ml/min; sodium hydroxide concentration: 100 mM; sodium acetate concentration: 0 min-0 mM, 2 min-0 mM and 20 min-20 mM.
(Catalase Formulation Containing Impure Enzymes within Predetermined Range)

In the present invention, a catalase formulation containing impure enzymes in a predetermined range may be used. Specifically, a catalase formulation in which the content ratio (B/A) of saccharification activity relative to catalase activity (A) in the catalase formulation is 0.005 or less is used. Preferably, B/A is 0.0045 or less, 0.003 or less, 0.002 or less, 0.0015 or less, 0.001 or less, 0.0005 or less or 0.0004 or less.

In addition, B/A is preferably 0.00002 or more, specifically may be 0.0001 or more, 0.0002 or more, 0.0003 or more or 0.0004 or more. Even if a catalase formulation has saccharification activity at this ratio, the main reaction, that is, carbohydrate oxidization, proceeds more quickly than the saccharification reaction, and therefore, use of such a catalase formulation is unlikely to result in reduction in yield.

Additionally, in the present invention, even when the content ratio (B/A) of saccharification activity (B) relative to catalase activity (A) in a catalase formulation is 0.005 or less, addition of an extra amount of the catalase formulation to a raw material carbohydrate sometimes causes impure enzymes in the catalase formulation to hydrolyze the raw material substrate, and as a result, a sugar carboxylic acid such as maltobionic acid may not be obtained in an expected composition. For this reason, the catalase formulation needs to be applied so that saccharification activity in the catalase formulation is 0.9 U/g or less (preferably 0.8 U/g or less, 0.7 U/g or less or 0.65 U/g or less) with respect to the amount of the reducing sugar (wt % per solid) in the raw material substrate.

Catalase activity (A) in a catalase formulation is preferably 5,000 U/ml or more, specifically 10,000 U/ml or more, 15,000 U/ml or more, 20,000 U/ml or more or 22,500 U/ml or more. Even when the saccharification activity is high to some extent, the high catalase activity is likely to keep the effect on the yield at a low level.

The catalase activity (A) in a catalase formulation is preferably 500,000 U/ml or less, and more specifically, may be 2,500,000 U/ml or less, 150,000 U/ml or less, 100,000 U/ml or less, and 75,000 U/ml or less. The low saccharification activity of the catalase formulation used in the present invention easily keeps an effect on the yield low, even though the catalase activity is not overly active.

Saccharification activity (B) in the catalase formulation is preferably 250 U/ml or less, and specifically may be 100 U/ml or less, 50 U/ml or less, 30 U/ml or less or 25 U/ml or less.

On the other hand, saccharification activity (B) in the catalase formulation may be within an allowable range, and may be preferably 0.1 U/ml or more, specifically 0.5 U/ml or more, 1.0 U/ml or more, 1.5 U/ml or more or 2.0 U/ml or more. This level of saccharification activity is unlikely to lead to reduction in yield, because the main reaction, that is, carbohydrate oxidization, proceeds more quickly than the saccharification reaction.

The saccharification activity in the catalase formulation may be in an allowable range, specifically 0.00008 U/g or more, preferably 0.0005 U/g or more, 0.001 U/g or more or 0.0015 U/g or more, with respect to the amount of reducing sugar in a raw material substrate (wt % per solid content). This level of saccharification activity is unlikely to lead to reduction in yield, because the main reaction, that is, saccharide oxidization, proceeds more quickly than the saccharification reaction.

In the production of a sugar carboxylic acid such as maltobionic acid, the catalase formulation is preferably present in an amount of 40 U/g or more and 1,000 U/g or less, more preferably in an amount of 60 U/g or more and 500 U/g or less, with respect to the amount of the reducing sugar (per solid content) in the raw material substrate. Since the saccharification activity in the catalase formulation is kept low in the present invention, the yield is not easily decreased even if a sufficient amount of the catalase formulation is used to suppress decomposition of the carbohydrate oxidase by hydrogen peroxide. In addition, since decomposition of a starch decomposition product or starch transfer reaction product having a degree of polymerization of 2 or more, which is a raw material by the saccharification activity, is suppressed, yield is less likely to decrease even in the carbohydrate oxidization which takes a certain period of time, so that no excessive catalase activity is required.

Note that the catalase activity in a catalase formulation is measured as follows. The measurement method follows procedures for titrating residual hydrogen peroxide after an enzyme reaction with sodium thiosulfate (Supervised by Michio Ozaki, Enzyme Use Handbook, 1985, Chijin Shokan pp. 404-410). That is, 5 ml of a substrate solution obtained by diluting a commercially available 30 wt % hydrogen peroxide to 800-fold with a 50 mM phosphate buffer solution (pH 7.0) is put in a container, and the container is placed in a constant temperature water bath at 30° C. for 15 minutes to obtain a constant temperature. To this, 1 ml of an analyte enzyme solution kept at 30° C. is added and 2 ml of 0.5 N sulfuric acid is added at exactly 5 minutes after the addition and shaken well to stop enzyme activity. To this, 1 ml of a 10% by weight solution of potassium iodide, 1 drop of a 1% ammonium molybdate and 5 drops of a 0.5% starch reagent as an indicator are added. This solution is titrated with 0.005 N sodium thiosulfate solution (for quantification) while stirring. For blank, 1 ml of water is added instead of the sample, and the amount of hydrogen peroxide decomposed by catalase action is calculated by subtracting the value of the analyte from the value of the blank and the catalase activity of the analyte enzyme solution is obtained from a standard curve. Note that 1 U refers to activity of decomposing 1 μmol of hydrogen peroxide per minute.

$$\text{Catalase activity}(U/ml) = A \times n$$

n: Dilution ratio

A: value A of x-axis of $y=(T_0-T_s)\times 24.18/T_0 \times 2.5 \times f$ is obtained from the graph of standard curve.

f: factor of 0.005 N sodium thiosulfate $T_0$: titration value (ml) of blank $T_s$: titration value of a sample (ml)

$24.18/T_0$: corrected value for change in activity measurement due to an initial substrate concentration 2.5:1 ml of a 0.005 N sodium thiosulfate solution corresponds to 2.5 μmol of hydrogen peroxide Saccharification activity defined in the present invention is power by which a starch decomposition product is hydrolyzed by glucoamylase activity and α-glucosidase activity to liberate glucose, and as for the saccharification activity of the present invention, 1 U can be defined as an activity of liberating 1 μmol of PNP per minute from 4-nitrophenyl β-maltoside (G2-(3-PNP) of the substrate.

Saccharification activity in a catalase formulation is determined by leaving the catalase formulation to react with 4-nitrophenyl β-maltoside to form 4-nitrophenyl β-glucoside, decomposing it with β-glucosidase to form 4-nitrophenol, and quantifying the 4-nitrophenol. Specifically, saccharification activity in a catalase formulation is measured using a saccharifying power measuring kit or a saccharifying power fractional quantification kit manufactured by Kikkoman Corporation.

(Measurement of Saccharifying Power Activity Using Saccharifying Power Measuring Kit Manufactured Kikkoman Corporation)

When using the Kikkoman's saccharifying power measuring kit, 0.5 ml of an enzyme solution containing β-glucosidase is added to 0.5 ml of a substrate solution containing 4-nitrophenyl β-maltoside. The resulting mixture is pre-warmed at 37° C. for 5 minutes, then 0.1 ml of a measurement sample is added and mixed, and left to react at 37° C. for 10 minutes. To stop the reaction, 2 ml of an enzyme stop solution containing sodium carbonate is added and mixed. The solution after the termination of the reaction is quantified at a wavelength of 400 nm to measure the saccharifying power, and the activity is calculated from the following calculation equation.

$$\text{Saccharification activity}(U/ml) = (Es-Eb) \times 0.171 \times n$$

Es: absorbance of measurement sample

Eb: absorbance of blank n: dilution ratio of enzyme solution

Sugar carboxylic acids prepared using the inventive method can be used in foods and beverages, cosmetics, pharmaceuticals, chemicals, and the like.

EXAMPLES

Test Example 1: Comparison of Carbonate Neutralizing Agent Addition Methods (Study of Addition Amount at the Start of the Treatment Step and Addition Methods During the Treatment Step)

Examples 1 to 3, and Comparative Example 1

Example 1

In a jar fermenter (capacity: 4 L, manufactured by Able Corporation), 1200 g of distilled water was added to 800 g of high-maltose starch syrup (Bx. 75%, manufactured by San-ei Sucrochemical Co., Ltd.) containing 1.2 wt % of glucose, 15.0 wt % of maltotriose and 13.5 wt % of maltooligosaccharide of maltotetraose (degree of polymerization: 4) or higher in addition to 70.3 wt % of maltose, and dissolved so as to be 30 wt %, followed by addition of 78 g (amount corresponding to 100% of the predetermined amount) of calcium carbonate (manufactured by Wako Pure Chemical Industries Co., Ltd.), 4.0 ml (1200 U, 2 U/g substrate) of an *Acremonium chrysogenum*-derived carbohydrate oxidase formulation (carbohydrate oxidation activity: 300 U/ml) and 1.56 ml (84,000 U, 140 U/g substrate) of a genus *Aspergillus*-derived catalase formulation E (catalase activity: 53,800 U/ml, saccharification activity: 2.2 U/ml, saccharification activity/catalase activity ratio=0.00004). Aeration agitation (continuous aeration from a pipe equipped with a sintered filter having a pore diameter of 10 μm) was carried out at 35° C. and 500 rpm at an air aeration of 1 L/min. At 4 hours after the start of the reaction, 4.0 ml of the carbohydrate oxidase agent (1200 U, 2 U/g substrate) was additionally added, and oxidation was carried out.

Note that the added amount of calcium carbonate at this time, 78 g, corresponds to 100% of the predetermined amount. Saccharification activity/catalase activity ratio was 0.00004 (i.e., 0.005 or less) and saccharification activity was 0.013 U/g (i.e., 0.9 U/g or less) with respect to the reducing sugar of the raw material substrate.

Example 2

As Example 2, oxidation was carried out under the same conditions as in Example 1 with regard to the raw material carbohydrates, the amount of enzymes, the reaction temperatures and the aeration conditions, while adding 78 g of calcium carbonate (an amount corresponding to 100% of the predetermined amount) in three portions (50% of the predetermined amount at the start of the treatment step, 40% of the predetermined amount after 8 hours, and 10% of the predetermined amount after 22 hours).

Example 3

As Example 3, oxidation was carried out under the same conditions as in Example 1 with regard to the raw material carbohydrates, the amount of enzymes, the reaction temperatures and the aeration conditions, while adding calcium carbonate (7.8 g) in a mass corresponding to 10% of the predetermined amount at the start of the treatment step, and then sequentially adding the calcium carbonate (70.2 g) in a mass corresponding to the remaining amount 90% from 1 hour after the start of the reaction onward as a 15 wt % solution so that the pH was adjusted to 6.0. Note that in the sequential addition, pH is measured in real time, and the neutralizing agent is added by using a micropump.

Comparative Example 1

As Comparative Example 1, oxidation was carried out under the same conditions as in Example 1 with regard to the raw material carbohydrates, the amount of enzymes, the reaction temperatures and the aeration conditions, while sequentially adding a 15 wt % calcium carbonate solution over the duration of the treatment step from the start of the treatment step so that the pH decreased to 6.0 due to the oxidation. Note that the added amount of calcium carbonate at the start of the treatment step in Comparative Example 1 was calculated from the recorded data of the micropump to be equivalent to 1% of the predetermined amount.

For change in the oxidation, an mount of a reducing sugar in the reaction solution was quantified by the Nelson-Somogyi method, and the conversion rate was calculated by the following formula.

(Amount of reducing sugar before reaction start−amount of reducing sugar of reaction liquid)/amount of reducing sugar before reaction start× 100=oxidation ratio (%)

Note that in Examples 1 to 3, the dissolved oxygen amount was confirmed to be 1 ppm or more throughout the treatment step.

TABLE 1

| | | Reaction time (hr) | | | | | | | | |
|---|---|---|---|---|---|---|---|---|---|---|
| | | 0 | 4 | 6 | 8 | 10 | 23 | 26 | 28 | 31 |
| Example 1 | Oxidation ratio (%) | 0 | 28.5 | 38.3 | 45.6 | 52.0 | 95.5 | 99.5 | 100 | — |
| | pH | 8.04 | 6.54 | 6.41 | 6.38 | 6.38 | 6.07 | 6.21 | 6.55 | — |
| | Dissolved oxygen (ppm) | 7.09 | 4.63 | 2.69 | 2.80 | 2.80 | 6.09 | 6.63 | 7.12 | — |
| Example 2 | Oxidation ratio (%) | 0 | 25.8 | 36.1 | 45.6 | 54.7 | 89.2 | 95.8 | 98.7 | 100 |
| | pH | 7.84 | 6.48 | 6.23 | 6.03 | 6.53 | 6.45 | 7.07 | 7.07 | 7.08 |
| | Dissolved oxygen (ppm) | 7.17 | 4.15 | 2.74 | 3.14 | 3.64 | 6.64 | 6.85 | 6.96 | 6.98 |
| Example 3 | Oxidation ratio (%) | 0 | 20.3 | 31.8 | 41.8 | 51.4 | 86.0 | 89.8 | 91.9 | 95.1 |
| | pH | 7.60 | 6.00 | 6.00 | 6.00 | 6.00 | 6.00 | 6.00 | 6.00 | 6.00 |
| | Dissolved oxygen (ppm) | 7.25 | 3.72 | 2.75 | 3.21 | 3.75 | 6.69 | 6.43 | 6.51 | 6.87 |

TABLE 1-continued

| | | Reaction time (hr) | | | | | | | | |
|---|---|---|---|---|---|---|---|---|---|---|
| | | 0 | 4 | 6 | 8 | 10 | 23 | 26 | 28 | 31 |
| Comparative Example 1 | Oxidation ratio (%) | 0 | 17.1 | 26.5 | 33.6 | 40.4 | 73.4 | 79.1 | 84.0 | 86.9 |
| | pH | 6.00 | 6.00 | 6.00 | 6.00 | 6.00 | 6.00 | 6.00 | 6.00 | 6.00 |
| | Dissolved oxygen (ppm) | 7.18 | 4.51 | 2.61 | 2.71 | 3.16 | 6.36 | 6.71 | 6.76 | 6.92 |

As described above, with respect to Examples 1 to 3 in which calcium carbonate was added in an amount corresponding to 5% or more of the predetermined amount at the start of the treatment step, 100% was oxidized after 28 hours of the reaction in Example 1, after 31 hours of the reaction in Example 2, and 95% was oxidized after 31 hours of the reaction in Example 3, whereas in Comparative Example 1, in which an amount of calcium carbonate corresponding to 1% of the predetermined amount was added at the start of treatment step, and thereafter, pH was continuously adjusted by sequential addition, the oxidation ratio remained below 90% after 31 hours of the reaction. As a result, the reaction efficiency significantly changed.

Test Example 2: The Fourth Example Using a Carbonate Neutralizing Agent

Example 4

In a jar fermenter (capacity: 4 L, manufactured by Able Corporation), 1200 g of distilled water was added to 800 g of high-maltose starch syrup (Bx. 75%, manufactured by San-ei Sucrochemical Co., Ltd.) containing 1.2 wt % of glucose, 15.0 wt % of maltotriose and 13.5 wt % of maltooligosaccharide of maltotetraose (degree of polymerization: 4) or higher in addition to 70.3 wt % of maltose, and dissolved so as to be 30 wt %, followed by addition of 63 g (amount corresponding to 100% of the predetermined amount) of magnesium carbonate (manufactured by Wako Pure Chemical Industries Co., Ltd.), 4.0 ml (1200 U, 2 U/g substrate) of an *Acremonium chrysogenum*-derived carbohydrate oxidase formulation (carbohydrate oxidation activity: 300 U/ml) and 1.56 ml (84,000 U, 140 U/g substrate) of a genus *Aspergillus*-derived catalase formulation E (catalase activity: 53,800 U/ml, saccharification activity: 2.2 U/ml, saccharification activity/catalase activity ratio=0.00004). Aeration agitation (continuous aeration from a pipe equipped with a sintered filter having a pore diameter of 10 μm) was carried out at 35° C. and 300 rpm at an air aeration of 2 L/min. Additionally, at four hours after the start of the reaction, 4.0 ml of the carbohydrate oxidase agent (1200 U, 2 U/g substrate) was additionally added, and oxidation was carried out. Note that saccharification activity/catalase activity ratio at this time was 0.00004 (i.e., 0.005 or less) and saccharification activity was 0.013 U/g (i.e., 0.9 U/g or less) with respect to the reducing sugar of the raw material substrate.

For change in the oxidation, an amount of a reducing sugar of the reaction solution was quantified by the Nelson-Somogyi method, and the conversion rate was calculated by the following formula.

(Amount of reducing sugar before reaction start−amount of reducing sugar of reaction liquid)/amount of reducing sugar before reaction start×100=oxidation ratio (%)

TABLE 2

| | Reaction time (hr) | | | | | | |
|---|---|---|---|---|---|---|---|
| Example 4 | 0 | 4 | 6 | 10 | 22 | 24 | 28 |
| Oxidation ratio (%) | 0 | 27.0 | 38.0 | 54.3 | 96.9 | 98.5 | 100 |
| pH | 9.25 | 7.63 | 7.60 | 7.52 | 7.45 | 7.59 | 7.72 |

In Example 4, in which magnesium carbonate in an amount corresponding to 100% of the predetermined amount was added as the neutralizing agent at the start of the treatment step, the oxidation proceeded with pH change around 7.5, and 100% was oxidized after 28 hours.

Note that in Example 4, the dissolved oxygen amount was confirmed to be 1 ppm or more throughout the treatment step.

Test Example 3: Example in which a Hydrogen Carbonate Neutralizing Agent is Used and Comparative Example

Example 5, and Comparative Example 2

In a jar fermenter (capacity: 4 L, manufactured by Able Corporation), 1466 g of distilled water was added to 534 g of high-maltose starch syrup (Bx. 75%, manufactured by San-ei Sucrochemical Co., Ltd.) containing 1.2 wt % of glucose, 15.0 wt % of maltotriose and 13.5 wt % of maltooligosaccharide of maltotetraose (degree of polymerization: 4) or higher in addition to 70.3 wt % of maltose, and dissolved so as to be 20 wt %, followed by addition of 50 g (amount corresponding to 100% of the predetermined amount) of sodium hydrogen carbonate (manufactured by Wako Pure Chemical Industries Co., Ltd.), 2.67 ml (800 U, 2 U/g substrate) of an *Acremonium chrysogenum*-derived carbohydrate oxidase formulation (carbohydrate oxidation activity: 300 U/ml) and 1.04 ml (56,000 U, 140 U/g substrate) of a genus *Aspergillus*-derived catalase formulation E (catalase activity: 53,800 U/ml, saccharification activity: 2.2 U/ml, saccharification activity/catalase activity ratio=0.00004). Aeration agitation (continuous aeration from a pipe equipped with a sintered filter having a pore diameter of 10 μm) was carried out at 35° C. and 300 rpm at an air aeration of 2 L/min. At 4 hours after the start of the reaction, 2.67 ml of the carbohydrate oxidase agent (800 U, 2 U/g substrate) was additionally added, and oxidation was carried out. Note that saccharification activity/catalase activity ratio at this time was 0.00004 (i.e., 0.005 or less) and saccharification activity was 0.013 U/g (i.e., 0.9 U/g or less) with respect to the reducing sugar of the raw material substrate.

As Comparative Example 2, oxidation was carried out under the same conditions as in Example 5 with regard to the raw material carbohydrates, the amount of enzymes, the reaction temperatures and the aeration conditions, while sequentially adding a 25 wt % sodium hydroxide solution over the course of the treatment step from the start of the treatment step so that the pH decreased to 9.5 due to the oxidation.

For change in the oxidation, an amount of a reducing sugar of the reaction solution was quantified by the Nelson-Somogyi method, and the conversion rate was calculated by the following formula.

(Amount of reducing sugar before reaction start−
amount of reducing sugar of reaction liquid)/
amount of reducing sugar before reaction start×
100=oxidation ratio (%)

TABLE 3

|  |  | Reaction time (hr) | | | | | | |
|---|---|---|---|---|---|---|---|---|
|  |  | 0 | 4 | 6 | 20 | 23 | 26 | 28 |
| Example 5 | Oxidation ratio (%) | 0 | 24.5 | 35.1 | 79.4 | 90.3 | 97.5 | 100 |
|  | pH | 9.72 | 9.94 | 9.88 | 9.70 | 9.71 | 9.73 | 9.90 |
| Comparative Example 2 | Oxidation ratio (%) | 0 | 27.6 | 37.4 | 57.5 | 58.3 | 58.8 | 59.1 |
|  | pH | 9.50 | 9.50 | 9.50 | 9.50 | 9.50 | 9.50 | 9.50 |

In Example 5, in which sodium hydrogen carbonate in an amount corresponding to 100% of the predetermined amount was added as the neutralizing agent at the start of the treatment step, oxidation proceeded with pH change around 9.8, and 100% was oxidized after 28 hours. Meanwhile, in Comparative Example 2, in which sodium hydroxide, which is a basic compound with a pKb less than 1 was added, although pH was lower both at the beginning of the reaction and during the reaction compared to in Example 5, the oxidation ratio after 28 hours remained less than 60%. This was a very low value in the oxidation ratio, that is, yield in industrial production. In other words, it can be understood that a basic compound with a pKb less than 1 is unsuitable for industrial production as the basic compound to be added at the start of the treatment step, though the compound is a basic compound.

Note that in Example 5, the dissolved oxygen amount was confirmed to be 1 ppm or more throughout the treatment step.

Test Example 4: Combination Use (I) of a Carbonate Neutralizing Agent and a Basic Compound Neutralizing Agent Example 6

In a jar fermenter (capacity: 4 L, manufactured by Able Corporation), 1200 g of distilled water was added to 800 g of high-maltose starch syrup (Bx. 75%, manufactured by San-ei Sucrochemical Co., Ltd.) containing 1.2 wt % of glucose, 15.0 wt % of maltotriose and 13.5 wt % of maltooligosaccharide of maltotetraose (degree of polymerization: 4) or higher in addition to 70.3 wt % of maltose, and dissolved so as to be 30 wt %, followed by addition of 39 g, which corresponds to 50% of the predetermined amount, of calcium carbonate (manufactured by Wako Pure Chemical Industries Co., Ltd.), 4.0 ml (1200 U, 2 U/g substrate) of an *Acremonium chrysogenum*-derived carbohydrate oxidase formulation (carbohydrate oxidation activity: 300 U/ml) and 1.56 ml (84,000 U, 140 U/g substrate) of a genus *Aspergillus*-derived catalase formulation E (catalase activity: 53,800 U/ml, saccharification activity: 2.2 U/ml, saccharification activity/catalase activity ratio=0.00004). Aeration agitation (continuous aeration from a pipe equipped with a sintered filter having a pore diameter of 10 μm) was carried out at 35° C. and 300 rpm at an air aeration of 1 L/min. At 4 hours after the start of the reaction, 4.0 ml of the carbohydrate oxidase agent (1200 U, 2 U/g substrate) was additionally added, and oxidation was carried out. Note that saccharification activity/catalase activity ratio at this time was 0.00004 (i.e., 0.005 or less) and saccharification activity was 0.013 U/g (i.e., 0.9 U/g or less) with respect to the reducing sugar of the raw material substrate.

Further, oxidation was carried out, while sequentially adding a 25 wt % calcium hydroxide solution in an amount corresponding to the remaining amount 50% of the predetermined amount from 8 hours after the start of the reaction onward so that the pH became 7.0.

For change in the oxidation, an amount of a reducing sugar of the reaction solution was quantified by the Nelson-Somogyi method, and the conversion rate was calculated by the following formula.

(Amount of reducing sugar before reaction start−
amount of reducing sugar of reaction liquid)/
amount of reducing sugar before reaction start×
100=oxidation ratio (%)

TABLE 4

|  | Reaction time (hr) | | | | | | |
|---|---|---|---|---|---|---|---|
| Example 6 | 0 | 4 | 6 | 10 | 22 | 24 | 28 |
| Oxidation ratio (%) | 0 | 24.0 | 36.1 | 54.7 | 85.2 | 89.0 | 97.7 |
| pH | 7.84 | 6.48 | 6.23 | 7.00 | 7.00 | 7.00 | 7.00 |
| Dissolved oxygen (ppm) | 6.98 | 3.94 | 2.71 | 3.46 | 6.44 | 6.55 | 6.79 |

Calcium carbonate in an amount corresponding to 50% of the predetermined amount was added at the start of the treatment step, and then the addition method was switched to sequential addition of calcium hydroxide from 8 hours after the start of the reaction onward, but the reaction efficiently proceeded and 95% or more was oxidized after 28 hours.

Note that in Example 6, the dissolved oxygen amount was confirmed to be 1 ppm or more throughout the treatment step.

Test Example 5: Combination Use (II) of a Hydrogen Carbonate Neutralizing Agent and a Basic Compound Neutralizing Agent Example 7

In a jar fermenter (capacity: 4 L, manufactured by Able Corporation), 1200 g of distilled water was added to 800 g of high-maltose starch syrup (Bx. 75%, manufactured by San-ei Sucrochemical Co., Ltd.) containing 1.2 wt % of glucose, 15.0 wt % of maltotriose and 13.5 wt % of maltooligosaccharide of maltotetraose (degree of polymerization: 4) or higher in addition to 70.3 wt % of maltose, and dissolved so as to be 30 wt %, followed by addition of 37 g, which corresponds to 50% of the predetermined amount, of sodium hydrogen carbonate (manufactured by Wako Pure Chemical Industries Co., Ltd.), 4.0 ml (1200 U, 2 U/g substrate) of an *Acremonium chrysogenum*-derived carbohydrate oxidase formulation (carbohydrate oxidation activity: 300 U/ml) and 1.56 ml (84,000 U, 140 U/g substrate) of a genus *Aspergillus*-derived catalase formulation E (catalase activity: 53,800 U/ml, saccharification activity: 2.2 U/ml, saccharification activity/catalase activity ratio=0.00004). Aeration agitation (continuous aeration from a pipe equipped with a sintered filter having a pore diameter of 10 μm) was carried out at 35° C. and 300 rpm at an air aeration of 1 L/min. At 4 hours after the start of the reaction, 4.0 ml of the carbohydrate oxidase agent (1200 U, 2 U/g substrate) was additionally added, and oxidation was carried out. Note that saccharification activity/catalase activity ratio at this time was 0.00004 (i.e., 0.005 or less) and saccharification activity was 0.013 U/g (i.e., 0.9 U/g or less) with respect to the reducing sugar of the raw material substrate.

Further, oxidation was carried out while sequentially adding a 25 wt % sodium hydroxide solution in an amount corresponding to the remaining amount 50% from 8 hours after the start of the reaction onward so that the pH became 7.0.

For change in the oxidation, an amount of a reducing sugar of the reaction solution was quantified by the Nelson-Somogyi method, and the conversion rate was calculated by the following formula.

(Amount of reducing sugar before reaction start−
amount of reducing sugar of reaction liquid)/
amount of reducing sugar before reaction start×
100=oxidation ratio (%)

TABLE 5

| | Reaction time (hr) | | | | | | |
|---|---|---|---|---|---|---|---|
| Example 7 | 0 | 4 | 6 | 10 | 22 | 26 | 32 |
| Oxidation ratio (%) | 0 | 23.2 | 34.4 | 49.6 | 76.5 | 86.0 | 95.2 |
| pH | 8.60 | 8.34 | 6.98 | 7.00 | 7.00 | 7.00 | 7.00 |
| Dissolved oxygen (ppm) | 6.93 | 3.84 | 2.73 | 4.17 | 6.24 | 6.45 | 6.64 |

Sodium hydrogen carbonate in an amount corresponding to 50% of the predetermined amount was added at the start of the treatment step, and then the addition method was switched to sequential addition of sodium hydroxide from 8 hours after the start of the reaction onward, but the reaction efficiently proceeded and 95% or more was oxidized after 32 hours.

Note that in Example 7, the dissolved oxygen amount was confirmed to be 1 ppm or more throughout the treatment step.

Test Example 5: Comparison of Dissolved Oxygen Amount and Yield by Difference in Stirring and Aeration Methods Example 8, Example 9, Comparative Example 3

In a jar fermenter (capacity: 4 L, manufactured by Able Corporation), 1200 g of distilled water was added to 800 g of high-maltose starch syrup (Bx. 75%, manufactured by San-ei Sucrochemical Co., Ltd.) containing 1.2 wt % of glucose, 15.0 wt % of maltotriose and 13.5 wt % of maltooligosaccharide of maltotetraose (degree of polymerization: 4) or higher in addition to 70.3 wt % of maltose, and dissolved so as to be 30 wt %, followed by addition of 78 g of calcium carbonate (manufactured by Wako Pure Chemical Industries Co., Ltd.), 4.0 ml (1200 U, 2 U/g substrate) of an *Acremonium chrysogenum* derived carbohydrate oxidase formulation (carbohydrate oxidation activity: 300 U/ml) and 1.56 ml (84,000 U, 140 U/g substrate) of a genus *Aspergillus*-derived catalase formulation E (catalase activity: 53,800 U/ml, saccharification activity: 2.2 U/ml, saccharification activity/catalase activity ratio=0.00004), and oxidation was performed at 35° C. by continuous aeration from a pipe equipped with a sintered filter having a pore diameter of 10 μm and agitation by a stirrer. Further, at four hours after the start of the reaction, 4.0 ml of the carbohydrate oxidase agent (1200 U, 2 U/g substrate) was additionally added. Influence by change in dissolved oxygen resulting from changing conditions for agitation by aeration was evaluated. Note that saccharification activity/catalase activity ratio at this time was 0.00004 (i.e., 0.005 or less) and saccharification activity was 0.013 U/g (i.e., 0.9 U/g or less) with respect to the reducing sugar of the raw material substrate.

For change in the oxidation, an amount of a reducing sugar of the reaction solution was quantified by the Nelson-Somogyi method, and the conversion rate was calculated by the following formula.

(Amount of reducing sugar before reaction start−
amount of reducing sugar of reaction liquid)/
amount of reducing sugar before reaction start×
100=oxidation ratio (%)

TABLE 6

| | Agitation/air aeration | | | Time (hr) | | | | | | | |
|---|---|---|---|---|---|---|---|---|---|---|---|
| | | | | 0 | 4 | 6 | 8 | 10 | 23 | 26 | 28 |
| Example 8 | 500 rpm | | Oxidation ratio (%) | 0.0 | 28.5 | 38.3 | 45.6 | 52.0 | 95.5 | 99.5 | 100 |
| | 1.0 L/min. | | Dissolved oxygen (ppm) | 7.09 | 4.63 | 2.69 | 2.8 | 2.8 | 6.09 | 6.63 | 7.12 |
| Example 9 | 300 rpm | | Oxidation ratio (%) | 0.0 | 25.4 | 35.8 | 41.7 | 47.6 | 91.5 | 95.7 | 98.9 |
| | 1.0 L/min. | | Dissolved oxygen (ppm) | 7.06 | 3.21 | 1.84 | 1.86 | 1.89 | 2.74 | 4.8 | 5.9 |
| Comparative Example 3 | 200 rpm | | Oxidation ratio (%) | 0.0 | 6.8 | 9.0 | 12.4 | 13.1 | 31.5 | 35.4 | 43.0 |
| | 0.5 L/min. | | Dissolved oxygen (ppm) | 6.79 | 0.37 | 0.43 | 0.76 | 0.84 | 0.87 | 0.90 | 1.10 |

As a result of the test, as can be seen in Examples 8 and 9, a dissolved oxygen amount of 1 ppm or more in the stage until 10 hours after the start of the reaction allowed oxidation of 95% or more at 26 hours after the start of the reaction, whereas in Comparative Example 3, the dissolved oxygen amount varied at a level of 1 ppm or less and the oxidation ratio remained at about 43% in the stage at 28 hours after the start of the reaction.

Test Example 6: Application Example in which Reactor with Large Capacity was Used and Total Amount of Reaction Liquid was 1 Ton or More Example 10

In an SUS type reactor with a jacket (capacity: 10,000 L, manufactured by Yashima Chemical Engineering Co., Ltd.) equipped with a horizontal type 2.2 kW propeller wing type stirrer (manufactured by Takeuchi MFG. Co. Ltd.), 4.4 tons of tap water was added to 3.3 tons of high-maltose starch syrup (Bx. 70%, manufactured by San-ei Sucrochemical Co., Ltd.) containing 1.2 wt % of glucose, 15.0 wt % of maltotriose and 13.5 wt % of maltooligosaccharide of maltotetraose (degree of polymerization: 4) or higher in addition to 70.3 wt % of maltose, and dissolved so as to be 30 wt %, followed by addition of 300 kg (amount corresponding to 100% of the predetermined amount) of calcium carbonate (manufactured by Sankyo Seifun), 14.6 L (4,599,945 U, 2 U/g substrate) of an *Acremonium chrysogenum*-derived carbohydrate oxidase formulation (carbohydrate oxidation activity: 315 U/ml) and 3.385 L (231,000,000 U, 100 U/g substrate) of a genus *Aspergillus*-derived catalase formulation F (catalase activity: 68,250 U/ml, saccharification activity: 23.6 U/ml, saccharification activity/catalase activity ratio=0.000035). Aeration agitation (continuous aeration from a fine bubble generator) was carried out at 35° C. and 200 rpm at an air aeration of 800 L/min. At 12 hours and 24 hours after the start of the reaction, 3.651 L of the carbohydrate oxidase agent (1,150,065 U, 0.5 U/g substrate) and 0.677 L of the catalase formulation (46,200,000 U, 20 U/g substrate) were respectively formulated, and oxidation was carried out. Note that saccharification activity/catalase activity ratio at this time was 0.000346 (i.e., 0.005 or less) and saccharification activity was 0.11 U/g (i.e., 0.9 U or less) with respect to the reducing sugar of the raw material substrate.

For change of the oxidation, an amount of a reducing sugar of the reaction solution was quantified by the Nelson-Somogyi method, and the conversion rate was calculated by the following formula.

(Amount of reducing sugar before reaction start−
amount of reducing sugar of reaction liquid)/
amount of reducing sugar before reaction start×
100=oxidation ratio (%)

TABLE 7

| | Reaction time (hr) | | | | | | |
|---|---|---|---|---|---|---|---|
| Example 10 | 0 | 6 | 12 | 24 | 30 | 36 | 42 |
| Oxidation ratio (%) | 0 | 25.0 | 44.7 | 81.4 | 91.7 | 95.5 | 98.6 |
| Dissolved oxygen (ppm) | 7.2 | 3.8 | 4.5 | 5.1 | 5.6 | 5.9 | 6.3 |

With regard to Example 10, oxidation ratios and dissolved oxygen amounts at times elapsed since the start of the oxidation to 42 hours are indicated in Table 7. As is shown in Table 7, even when a total amount of the reaction liquid was about 8 tons, addition of calcium carbonate as the neutralizing agent in advance and aeration so that dissolved oxygen amount was 1 ppm or more allowed neutralization to effectively proceed, and the oxidation proceeded to 98.6% at 42 hours after the start of the reaction. The effect of the present invention was confirmed even in a reaction system of industrial production level.

Test Example 7: Application Example in which Reactor with Large Capacity was Used and Total Amount of Reaction Liquid was 1 Ton or More Example 11, 12 and Comparative Example 4

Example 11

In an SUS reactor with a jacket (capacity: 10,000 L, manufactured by Yashima Chemical Engineering Co., Ltd.) equipped with a horizontal type 2.2 kW propeller wing type stirrer (manufactured by Takeuchi MFG. Co. Ltd.), 4.4 tons of tap water was added to 3.3 tons of high-maltose starch syrup (Bx. 70%, manufactured by San-ei Sucrochemical Co., Ltd.) containing 1.2 wt % of glucose, 15.0 wt % of maltotriose and 13.5 wt % of maltooligosaccharide of maltotetraose (degree of polymerization: 4) or higher in addition to 70.3 wt % of maltose, and dissolved so as to be 30 wt %, followed by addition of 300 kg (amount corresponding to 100% of the predetermined amount) of calcium carbonate (manufactured by Sankyo Seifun), 14.6 L (4599945 U, 2 U/g substrate) of *Acremonium chrysogenum* derived carbohydrate oxidase formulation (carbohydrate oxidation activity: 315 U/ml) and 3.385 L (231,000,000 U, 100 U/g substrate) of a genus *Aspergillus* derived catalase formulation F (catalase activity: 68,250 U/ml, saccharification activity: 23.6 U/ml, saccharification activity/catalase activity ratio=0.000035). Aeration agitation (continuous aeration from a fine bubble generator) was carried out at 35° C. and 200 rpm at an air aeration of 800 L/min. At 12 hours and 24 hours after the start of the reaction, 3.651 L of the carbohydrate oxidase agent (1,150,065 U, 0.5 U/g substrate) and 0.677 L of the catalase formulation (46,200,000 U, 20 U/g substrate) were respectively added, and oxidation was carried out. Note that saccharification activity/catalase activity ratio at this time was 0.000346 (i.e., 0.005 or less) and saccharification activity was 0.11 U/g (i.e., 0.9 U/g or less) with respect to the reducing sugar of the raw material substrate.

For change of the oxidation, an amount of a reducing sugar of the reaction solution was quantified by the Nelson-Somogyi method, and the conversion rate was calculated by the following formula.

(Amount of reducing sugar before reaction start−
amount of reducing sugar of reaction liquid)/
amount of reducing sugar before reaction start×
100=oxidation ratio (%)

TABLE 8

| | Reaction time (hr) | | | | | | |
|---|---|---|---|---|---|---|---|
| Example 11 | 0 | 6 | 12 | 24 | 30 | 36 | 42 |
| Oxidation ratio (%) | 0 | 25.0 | 44.7 | 81.4 | 91.7 | 95.5 | 98.6 |
| Dissolved oxygen (ppm) | 7.2 | 3.8 | 4.5 | 5.1 | 5.6 | 5.9 | 6.3 |

With regard to Example 11, oxidation ratios and dissolved oxygen amounts at times elapsed since the start of the oxidation to 42 hours are indicated in Table 8. As is shown in Table 8, even when a total amount of reaction liquid is about 8 tons, addition of calcium carbonate as the neutralizing agent in advance and aeration so that dissolve oxygen is 1 ppm or more allow neutralization to effectively proceed and the oxidation proceeded to 98.6% at 42 hours after the start of the reaction. The effect of the present invention was confirmed even in a reaction system of industrial production level.

Example 12

As Example 12, oxidation was carried out under the same conditions as in Example 12 with regard to the raw material carbohydrates, the amount of enzymes, the reaction temperatures and the aeration conditions, and calcium carbonate (210 kg) in a mass corresponding to 70% of the predetermined amount was added at the start of the treatment step. Then, oxidation was carried out while sequentially adding calcium hydroxide in a mass (39.7 kg) corresponding to the remaining amount 30% as a 15 wt % solution from 20 hours after the start of the reaction onward so that the pH became 5.5 to 7.5.

TABLE 9

| Example 12 | Reaction time (hr) | | | | | | |
|---|---|---|---|---|---|---|---|
| | 0 | 6 | 12 | 20 | 30 | 40 | 50 |
| Oxidation ratio (%) | 0 | 22.5 | 39.5 | 58.6 | 81.2 | 94.5 | 98.4 |
| Dissolved oxygen (ppm) | 7.2 | 4.1 | 5.0 | 5.3 | 5.4 | 5.8 | 6.1 |

With regard to Example 12, oxidation ratios and dissolved oxygen amounts with regard to times elapsed since the start of the oxidation to 50 hours are indicated in Table 9. As is shown in Table 9, even under conditions that: a total amount of the reaction liquid was about 8 tons, calcium carbonate in an amount corresponding to 70% of the predetermined amount was added at the start of the reaction, and the neutralization of the remainder corresponding to 30% was performed with calcium hydroxide, aeration so that dissolved oxygen amount was 1 ppm or more allowed neutralization to effectively proceed and the oxidation proceeded to 98.4% at 50 hours after the start of the reaction. The effect of the present invention was confirmed even in a reaction system of industrial production level.

Comparative Example 4

As Comparative Example 4, oxidation was carried out under the same conditions as in Example 11 with regard to the raw material carbohydrates, the amount of enzymes, the reaction temperatures and the aeration conditions, and calcium carbonate (6 kg) in a mass corresponding to 2% of the predetermined amount was added at the start of the treatment step. Then, oxidation was carried out while sequentially adding calcium hydroxide in a mass (129.5 kg) corresponding the remaining amount 98% as a 15 wt % solution from 1 hour after the start of the treatment step onward so that the pH became 5.5 to 7.5.

TABLE 10

| Comparative Example 4 | Reaction time (hr) | | | | | | |
|---|---|---|---|---|---|---|---|
| | 0 | 6 | 12 | 20 | 30 | 40 | 50 |
| Oxidation ratio (%) | 0 | 15.5 | 31.5 | 49.2 | 72.2 | 80.3 | 82.4 |
| Dissolved oxygen (ppm) | 7.2 | 4.1 | 5.0 | 5.3 | 5.4 | 5.8 | 6.5 |

In Comparative Example 4, in which calcium carbonate in an amount corresponding to 2% of the predetermined amount was added at the start of the treatment step and thereafter sodium hydroxide was sequential added to continuously adjust pH, the oxidation significantly lost speed from 40 hours after the start of the reaction onward and oxidation ratio remained at less than 90%. This result greatly differed from those of Examples 11 and 12 in reaction efficiency.

The invention claimed is:

1. A method for producing a sugar carboxylic acid in which an aldehyde group on a reducing end of a starch decomposition product or starch transfer reaction product having a degree of polymerization of 2 or more and having a glucose residue at the reducing end is oxidized,
   the method comprising a step of treating a raw material substrate containing the starch decomposition product or starch transfer reaction product in the presence of a catalase formulation with a carbohydrate oxidase agent producing hydrogen peroxide as a by-product in carbohydrate oxidation,
   the catalase formulation contains glucoamylase and α-glucosidase,
   wherein a total volume of a reaction liquid in the treatment step is 1 L or more, and
   wherein a carbonate or a hydrogen carbonate is added as a basic compound in a predetermined amount only at a start of the treatment step.

2. The method for producing a sugar carboxylic acid according to claim 1, wherein the carbonate has a solubility in water more than zero and 0.01 mol/L or less.

3. The method according to claim 1, wherein the carbonate is calcium carbonate, magnesium carbonate, dolomite or eggshell calcium.

4. The method for producing a sugar carboxylic acid according to claim 1, wherein oxygen is supplied during the treatment step so that a dissolved oxygen amount is 1 ppm or more.

5. The method for producing a sugar carboxylic acid according to claim 1, wherein oxygen is supplied so that a dissolved oxygen amount is 1 ppm or more in a time period during which oxidation ratio is from 0% to 50%, during the treatment step.

6. The method for producing a sugar carboxylic acid according to claim 1, wherein a content ratio (B/A) of saccharification activity (B) with respect to catalase activity (A) in the catalase formulation is 0.00002 or more and 0.005 or less, and
   wherein the saccharification activity is present in an amount of 0.9 U/g or less with respect to a reducing sugar in the raw material substrate.

7. The method for producing a sugar carboxylic acid according to claim 1, wherein a content ratio (B/A) of saccharification activity (B) with respect to catalase activity (A) in the catalase formulation is 0.005 or less, and the saccharification activity (B) is 0.1 U/ml or more, and wherein the saccharification activity is present in an amount of 0.9 U/g or less with respect to a reducing sugar in the raw material substrate.

8. The method for producing a sugar carboxylic acid according to claim 1, wherein a total amount of the reaction liquid in the treatment step is 50 kg or more.

9. The method for producing a sugar carboxylic acid according to claim 8, wherein the total amount of the reaction liquid in the treatment step is 1 ton or more.

10. The method for producing a carboxylic acid according to claim 1, wherein the sugar carboxylic acid is maltobionic acid.

11. The method for producing a carboxylic acid according to claim 1, wherein the raw material substrate containing the starch decomposition product or starch transfer reaction product comprises maltose, maltotriose and maltooligosaccharide of maltotetraose (degree of polymerization: 4) or higher.

12. The method for producing a carboxylic acid according to claim 1,
wherein oxygen is supplied so that a dissolved oxygen amount is 1 ppm or more in a time period during which oxidation ratio is from 0% to 50%, during the treatment step, and
to decrease the aeration amount in a time period during which the oxidation ratio is 51% or more, during the treatment step.

13. The method for producing a carboxylic acid according to claim 1,
wherein oxygen is supplied so that a dissolved oxygen amount is 1 ppm or more and 7.5 ppm or less in a time period during which oxidation ratio is from 0% to 50%, during the treatment step.

14. A method for producing a sugar carboxylic acid in which an aldehyde group on a reducing end of a starch decomposition product or starch transfer reaction product having a degree of polymerization of 2 or more and having a glucose residue at the reducing end is oxidized,
the method comprising a step of treating a raw material substrate containing the starch decomposition product or starch transfer reaction product in the presence of a catalase formulation with a carbohydrate oxidase agent producing hydrogen peroxide as a by-product in carbohydrate oxidation,
the catalase formulation contains glucoamylase and α-glucosidase,
wherein a total volume of a reaction liquid in the treatment step is 1 L or more,
wherein a predetermined amount of a basic compound is added during the treatment step; and
wherein addition of the basic compound in the predetermined amount comprises
addition of a first basic compound which is a carbonate or a hydrogen carbonate in an amount by mass corresponding to 5% or more and less than 100% of the predetermined amount, at the start of the treatment step, and
addition of a second basic compound that is identical to or is different from the first basic compound in an amount by mass corresponding to a remaining amount obtained by subtracting an amount added at the start of the treatment step from the predetermined amount, during the treatment step at a time other than at the start of the treatment step, and
wherein oxygen is supplied so that a dissolved oxygen amount is 1 ppm or more and 7.5 ppm or less in a time period during which oxidation ratio is from 0% to 50%, during the treatment step.

15. The method for producing a carboxylic acid according to claim 14, wherein the raw material substrate containing the starch decomposition product or starch transfer reaction product comprises maltose, maltotriose and maltooligosaccharide of maltotetraose (degree of polymerization: 4) or higher.

16. A method for producing a sugar carboxylic acid in which an aldehyde group on a reducing end of a starch decomposition product or starch transfer reaction product having a degree of polymerization of 2 or more and having a glucose residue at the reducing end is oxidized,
the method comprising a step of treating a raw material substrate containing the starch decomposition product or starch transfer reaction product in the presence of a catalase formulation with a carbohydrate oxidase agent producing hydrogen peroxide as a by-product in carbohydrate oxidation,
the catalase formulation contains glucoamylase and α-glucosidase,
wherein a total volume of a reaction liquid in the treatment step is 1 L or more,
wherein a predetermined amount of a basic compound is added during the treatment step; and
wherein addition of the basic compound in the predetermined amount comprises
addition of a first basic compound which is a carbonate or a hydrogen carbonate in an amount by mass corresponding to 5% or more and less than 100% of the predetermined amount, at the start of the treatment step, and
addition of a second basic compound which is a hydroxide salt in an amount by mass corresponding to a remaining amount obtained by subtracting an amount added at the start of the treatment step from the predetermined amount, during the treatment step at a time other than at the start of the treatment step.

* * * * *